United States Patent

Momokawa

(10) Patent No.: US 11,871,814 B2
(45) Date of Patent: Jan. 16, 2024

(54) INSOLE-TYPE ELECTRONIC DEVICE AND CONTROL METHOD FOR INSOLE-TYPE ELECTRONIC DEVICE

(71) Applicant: NEC Corporation, Tokyo (JP)

(72) Inventor: Yuuki Momokawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 253 days.

(21) Appl. No.: 17/385,064

(22) Filed: Jul. 26, 2021

(65) Prior Publication Data

US 2022/0053872 A1 Feb. 24, 2022

(30) Foreign Application Priority Data

Aug. 24, 2020 (JP) ................................. 2020-141151

(51) Int. Cl.
| | |
|---|---|
| A43B 3/00 | (2022.01) |
| A43B 3/34 | (2022.01) |
| A61B 5/103 | (2006.01) |
| A61B 5/00 | (2006.01) |
| A43B 17/00 | (2006.01) |

(52) U.S. Cl.
CPC .............. *A43B 3/34* (2022.01); *A61B 5/0002* (2013.01); *A61B 5/1038* (2013.01); *A61B 5/6807* (2013.01); *A43B 17/00* (2013.01)

(58) Field of Classification Search
CPC ......... A43B 3/34; A43B 17/00; A61B 5/0002; A61B 5/1038; A61B 5/6807
USPC ......................................................... 73/172
See application file for complete search history.

(56) References Cited

U.S. PATENT DOCUMENTS

| | | | |
|---|---|---|---|
| 10,420,387 B2* | 9/2019 | Zambriski | A61B 5/0024 |
| 2011/0260857 A1* | 10/2011 | Hamill | A43B 17/00 |
| | | | 12/146 M |
| 2012/0159811 A1* | 6/2012 | Whitehead | A43B 3/38 |
| | | | 36/43 |
| 2015/0351664 A1* | 12/2015 | Ross | A43B 17/00 |
| | | | 702/44 |
| 2016/0313174 A1* | 10/2016 | Lightstone | A63B 24/0062 |
| 2020/0147382 A1* | 5/2020 | Caban | A61B 5/0024 |
| 2020/0147384 A1* | 5/2020 | Caban | A61N 1/36139 |
| 2021/0259579 A1* | 8/2021 | Grant-Beuttler | A61B 5/1038 |
| 2022/0296458 A1* | 9/2022 | Sugar | A61H 9/0078 |

FOREIGN PATENT DOCUMENTS

| | | |
|---|---|---|
| JP | 2006-204730 A | 8/2006 |
| JP | 2017-109062 A | 6/2017 |

\* cited by examiner

*Primary Examiner* — Max H Noori
(74) *Attorney, Agent, or Firm* — Sughrue Mion, PLLC

(57) ABSTRACT

To provide an insole-type electronic device that can be used in a location distant from a control unit and has small power consumption, the insole-type electronic device includes a first insole including a first sensor and a second insole including a second sensor. The first sensor acquires first sensor data relating to a biological activity of a first foot and the second sensor acquires second sensor data relating to a biological activity of a second foot. The first insole includes a first-sensor-data transmitter transmitting the first sensor to the second insole. The second insole includes a first-sensor-data receiver receiving the first sensor data, and a data processor processing the first sensor data and the second sensor data.

15 Claims, 10 Drawing Sheets

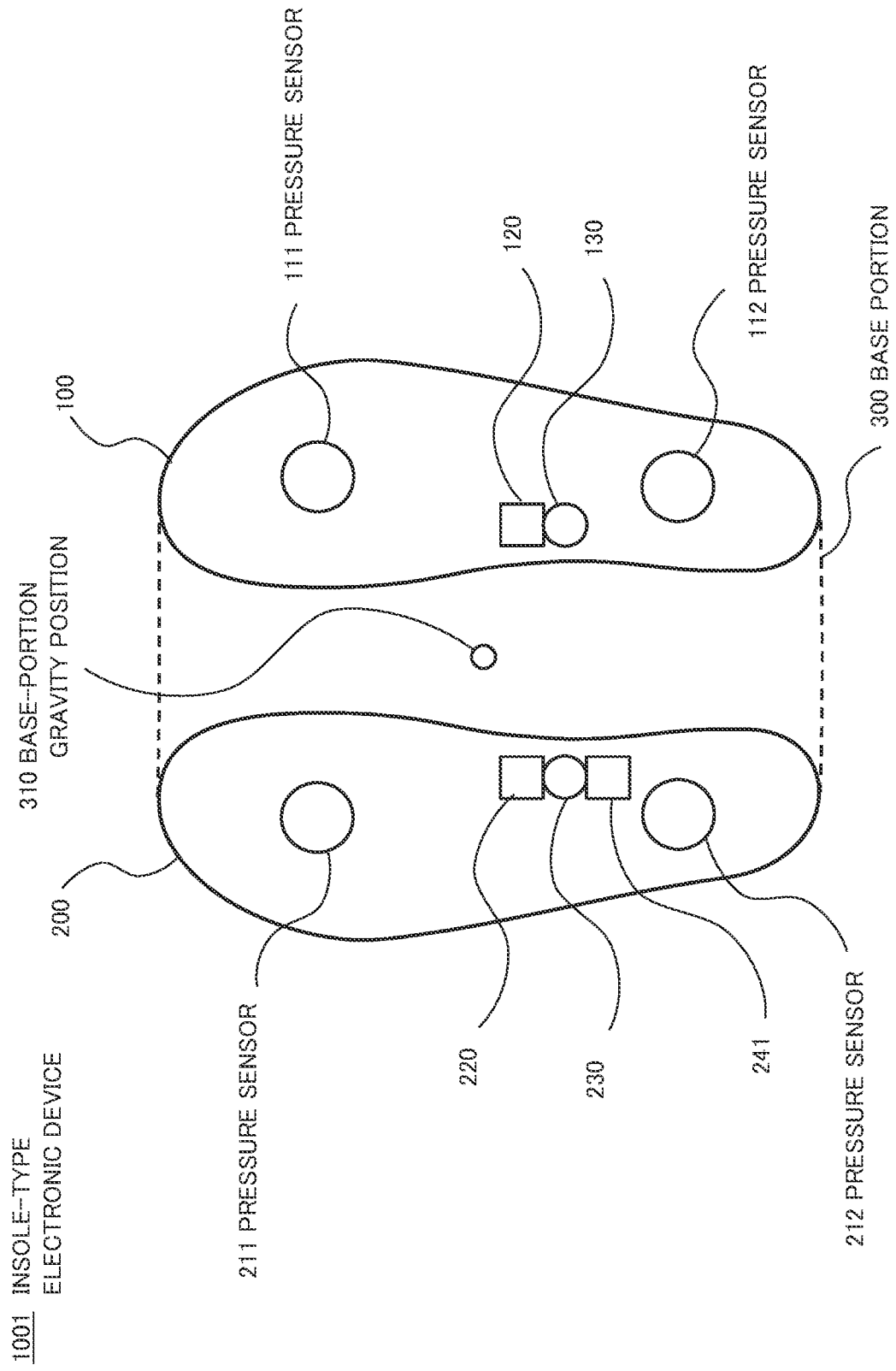

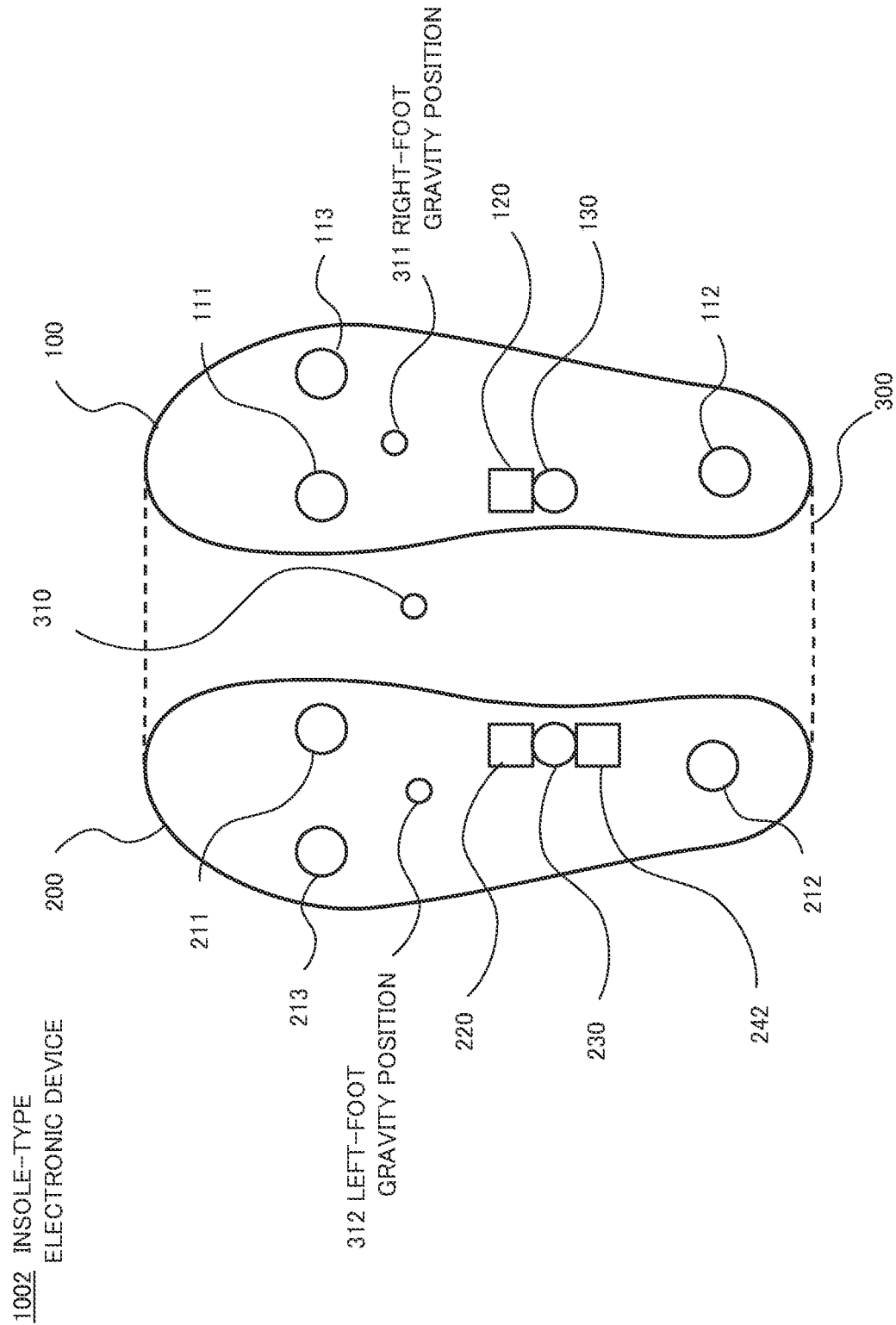

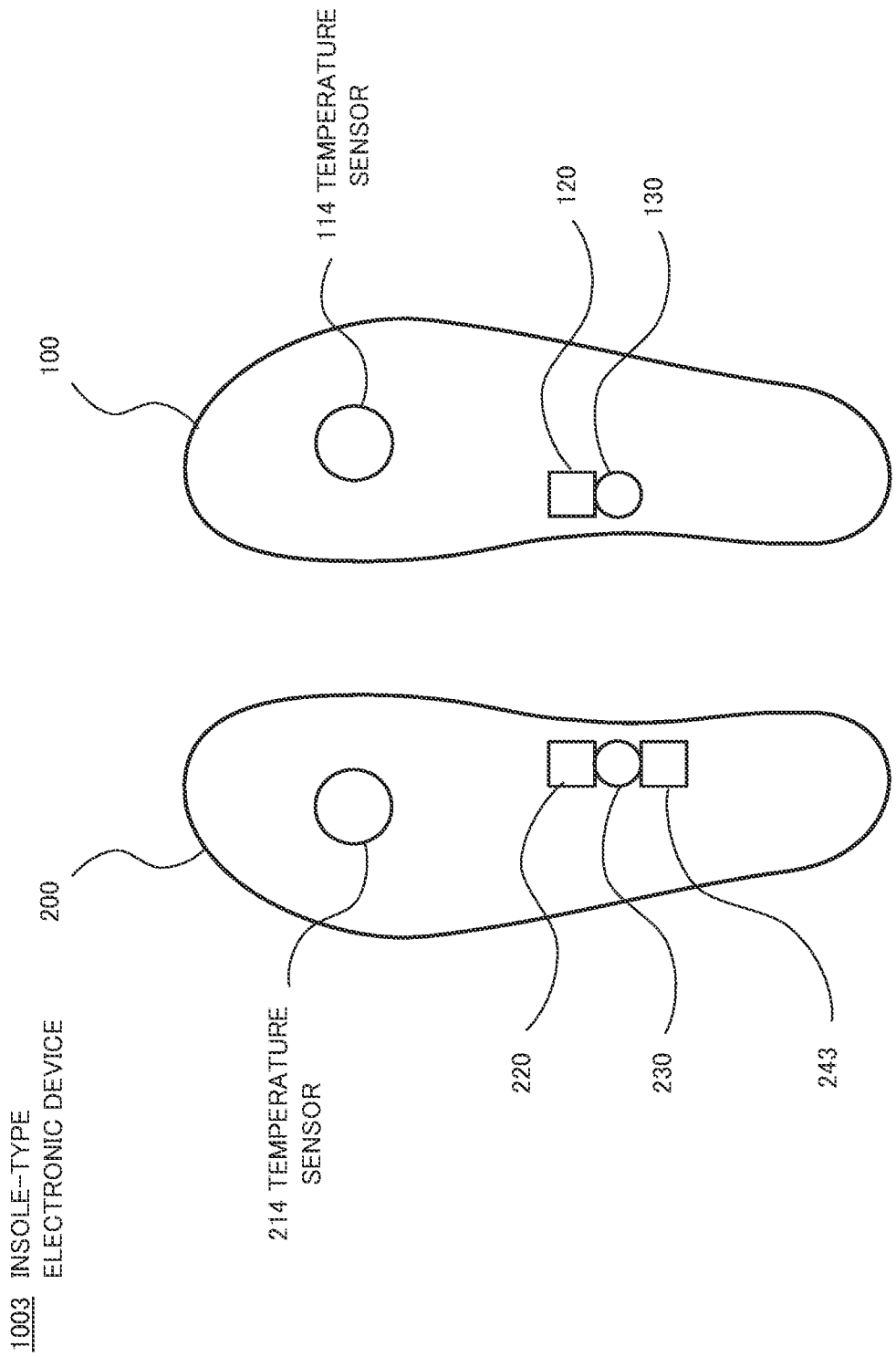

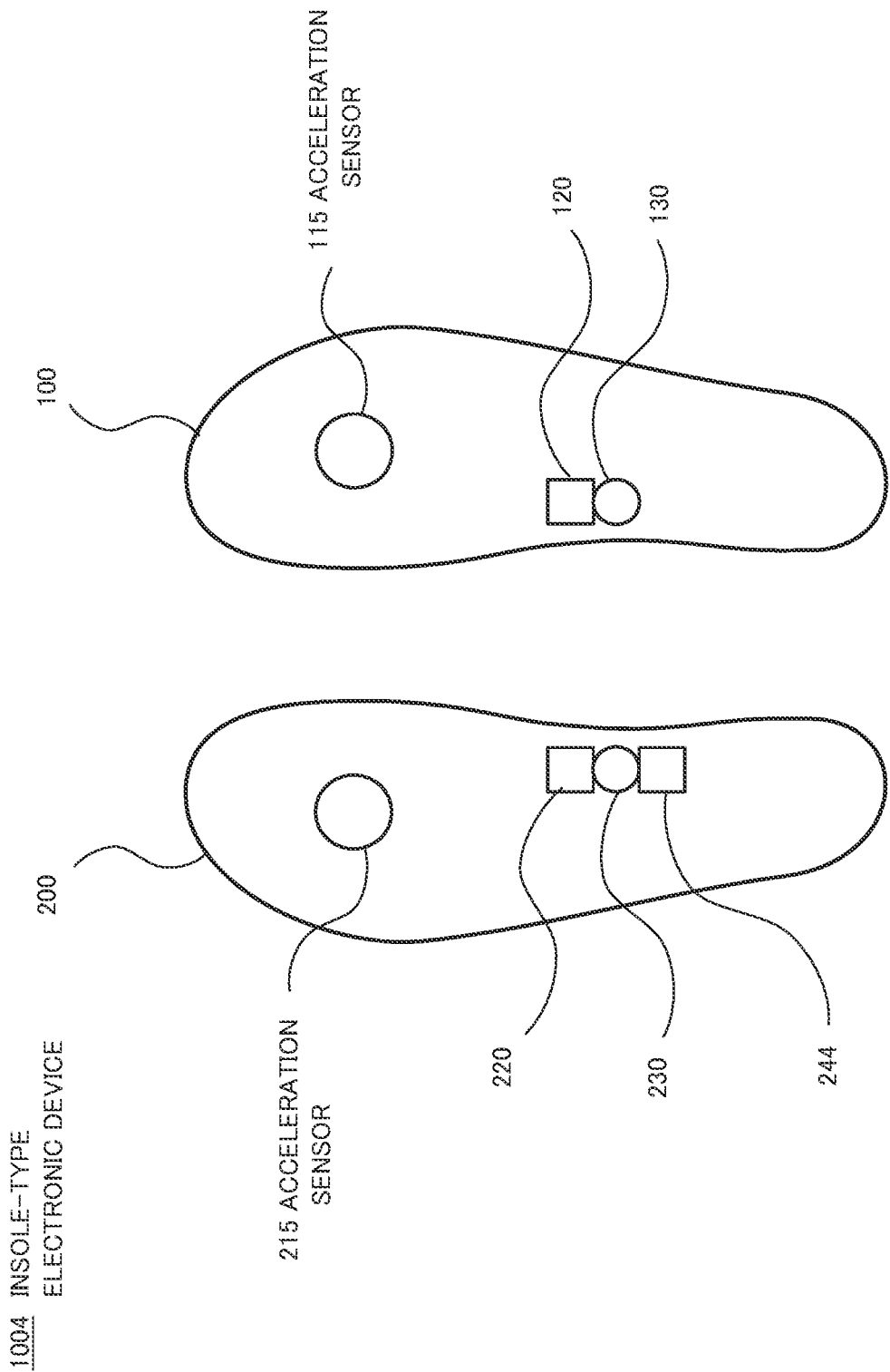

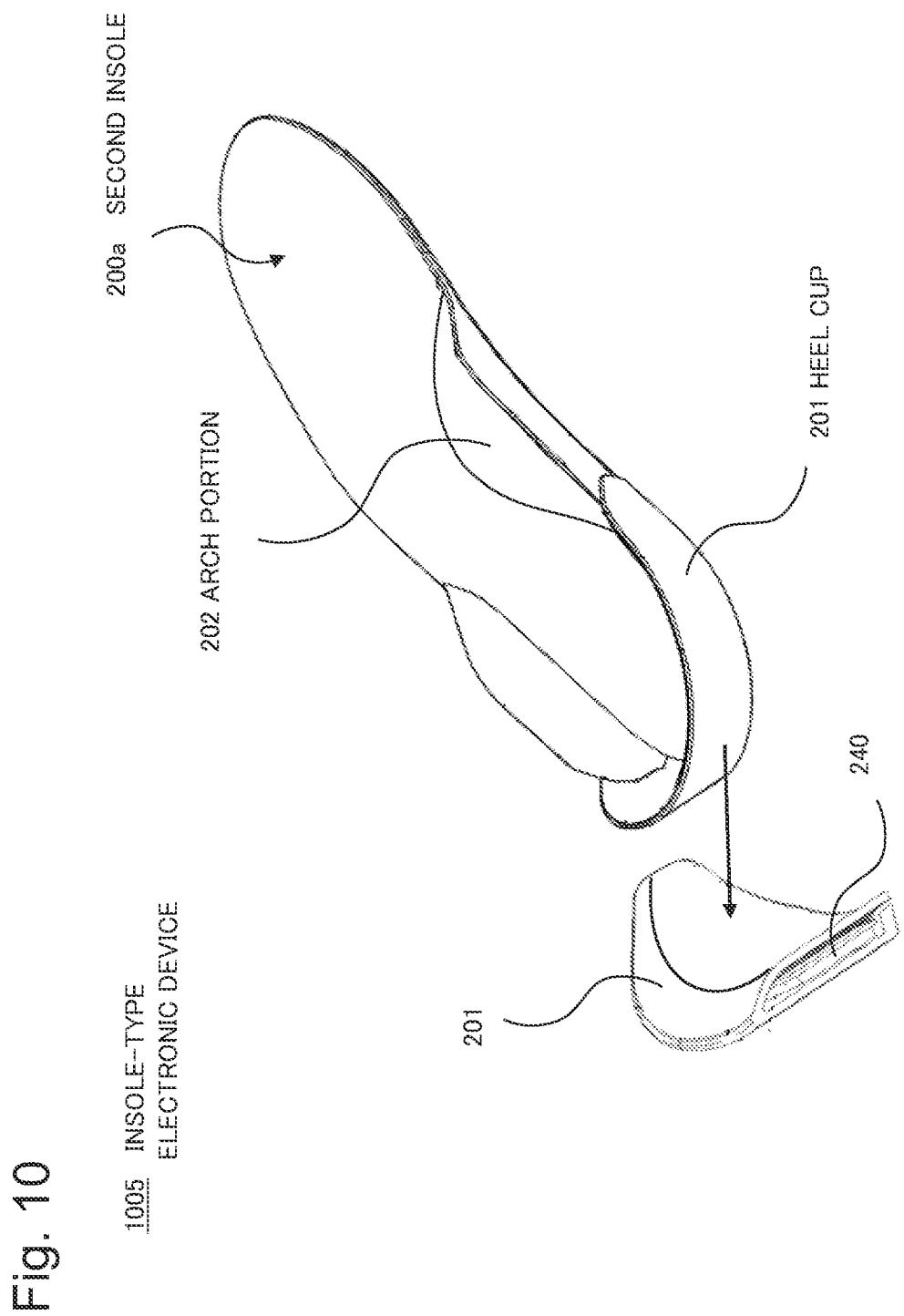

INSOLE-TYPE ELECTRONIC DEVICE AND CONTROL METHOD FOR INSOLE-TYPE ELECTRONIC DEVICE

This application is based upon and claims the benefit of priority from Japanese Patent Application No. 2020-141151, filed on Aug. 24, 2020, the disclosure of which is incorporated herein in its entirety by reference.

TECHNICAL FIELD

The present invention relates to an insole-type electronic device and a control method for an insole-type electronic device.

BACKGROUND ART

Recently, biological information, position information, and the like have been actively acquired by mounting an electronic device on a body. One mounting method for an electronic device is a method of incorporating an electronic device in shoes, and applications to crime prevention, prevention of accidents, rehabilitation support, advice about walking postures, sports, and the like using this method are expected.

PTL 1 (Japanese Unexamined Patent Application Publication No. 2006-204730), for example, discloses a technique for a walking-training support device in which a plurality of pressure-sensitive sensors are disposed in each of footwears such as shoes, insoles (sole inserts), and socks of both feet and a pressure applied to a sole is acquired. Output of each of the pressure-sensitive sensors is input, via a cable, to a control means such as a computer. The acquired pressure is analyzed, and thereby information useful for walking training, such as a pressure distribution of each sole portion and a body gravity position, can be acquired.

PTL 2 (Japanese Unexamined Patent Application Publication No. 2017-109062) discloses a technique for a walking training system in which a floor-reaction force sensor that measures a load applied on a sole surface of a foot and an acceleration sensor are disposed in a floor-reaction force unit that has a shape such as a shoe or an insole and is worn on a foot. Output of these sensors is transmitted, by using wireless communication, to a control unit provided in a system body. It is suggested that a degree of change in a walking pattern is determined from output of the acceleration sensor and dementia can be detected based on the degree.

SUMMARY

In the technique of PTL 1, a pressure-sensitive sensor disposed in a footwear is connected to a control means via a cable, and therefore there is a problem that the pressure-sensitive sensor can be used only near the control means.

In the technique of PTL 2, a wireless communication unit performing wireless communication to a control unit is provided on each of floor-reaction force units of both feet. Therefore, for use in a location distant from the control unit due to going out or the like, it is necessary to cause two wireless communication units capable of performing wireless communication having long reachable distance to operate. As a result, there is a problem that power consumption is large.

In view of the above-mentioned problems, the present invention has been made, and an object of the present invention is to provide an insole-type electronic device that can be used in a location distant from a control unit and has small power consumption.

In order to solve the above-mentioned problems, an insole-type electronic device according to the present invention includes a first insole including a first sensor and a second insole including a second sensor. The first sensor acquires first sensor data relating to a biological activity of a first foot, and the second sensor acquires second sensor data relating to a biological activity of a second foot. The first insole includes a first-sensor-data transmission means that transmits the first sensor data to the second insole. The second insole includes a first-sensor-data reception means that receives the first sensor data and a data processing means that processes the first sensor data and the second sensor data.

A control method for an insole-type electronic device according to the present invention includes acquiring, by using a first sensor disposed in a first insole and a second sensor disposed in a second insole, first sensor data and second sensor data relating to biological activities of a first foot and a second foot, respectively. The method further includes transmitting the first sensor data to the second insole and receiving, by the second insole, the first sensor data. The method further includes processing, by a data processing means included in the second insole, the first sensor data and the second sensor data.

An advantageous effect according to the present invention is to provide an insole-type electronic device that can be used in a location distant from a control unit and has small power consumption.

BRIEF DESCRIPTION OF THE DRAWINGS

Exemplary features and advantages of the present invention will become apparent from the following detailed description when taken with the accompanying drawings in which:

FIG. 6 is a block diagram illustrating an example 3 of the insole-type electronic device according to the second example embodiment;

FIG. 7 is a block diagram illustrating an example 4 of the insole-type electronic device according to the second example embodiment;

FIG. 8 is a block diagram illustrating an example 5 of the insole-type electronic device according to the second example embodiment;

FIG. 9 is a block diagram illustrating an example 6 of the insole-type electronic device according to the second example embodiment; and FIG. 10 is a perspective view illustrating an insole-type electronic device according to a third example embodiment.

EXAMPLE EMBODIMENT

Hereinafter, with reference to the accompanying drawings, example embodiments according to the present invention are described in detail. However, while according to the following example embodiments, technically preferable limitations are made in order to carry out the present invention, the scope of the invention is not limited to the following. Similar components in drawings are assigned with the same number and description therefor may be omitted.

First Example Embodiment

Figure 1:
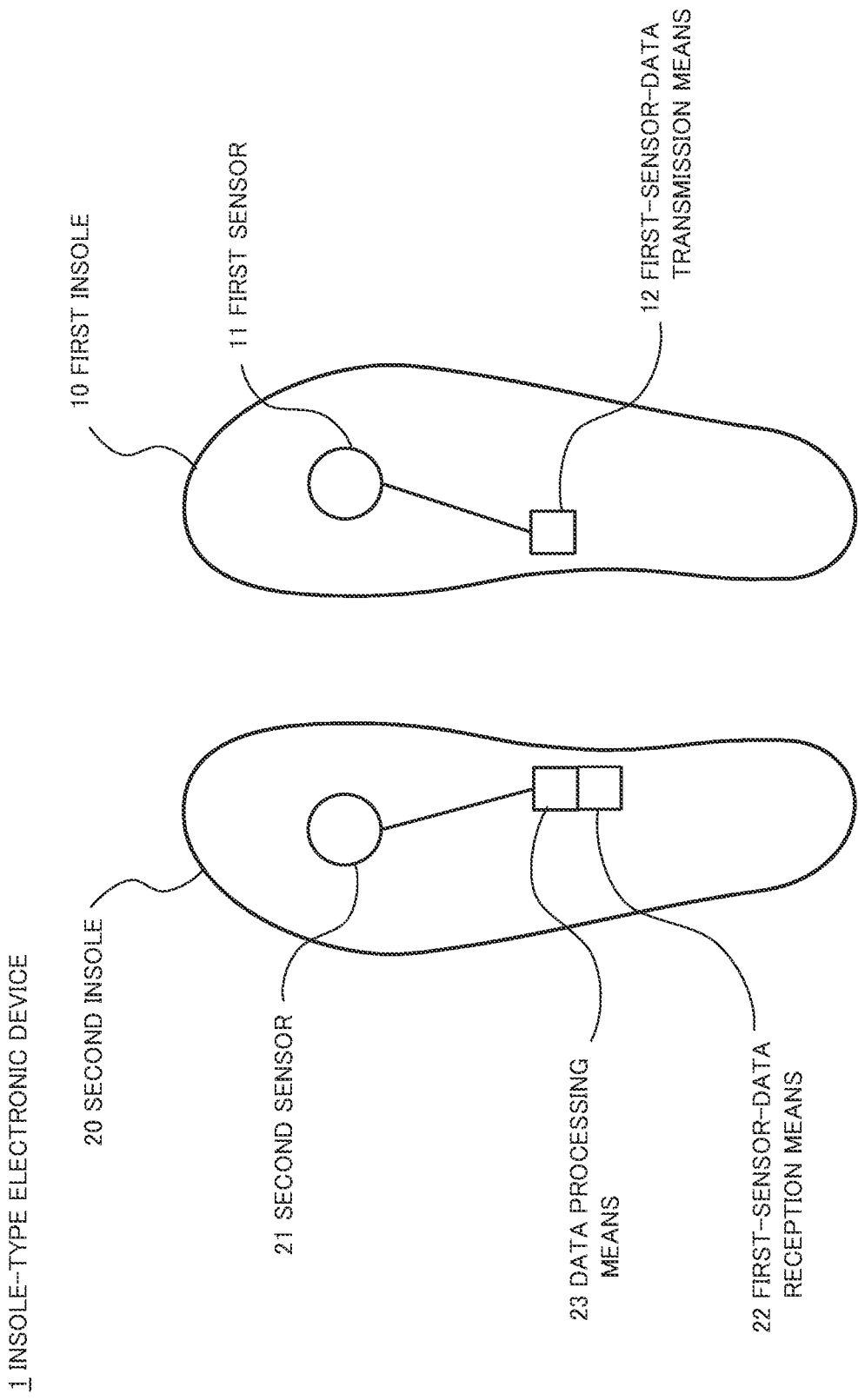
FIG. 1 is a block diagram illustrating an insole-type electronic device according to a first example embodiment.

FIG. 1 is a block diagram illustrating an insole-type electronic device 1 according to the present example embodiment. The insole-type electronic device 1 includes a first insole 10 including a first sensor 11 and a second insole 20 including a second sensor 21. The first sensor 11 acquires, as first sensor data, a signal relating to a biological activity occurring in a first foot, and the second sensor 21 acquires, as second sensor data, a signal relating to a biological activity occurring in a second foot. Herein, a signal relating to a biological activity includes, for example, a load applied to a sole, a temperature of a foot, and an acceleration of a foot.

The first insole 10 includes a first-sensor-data transmission means 12 that transmits first sensor data to the second insole 20. The second insole 20 includes a first-sensor-data reception means 22 that receives first sensor data and a data processing means 23 that processes the first sensor data and second sensor data.

According to the configuration, the first-sensor-data transmission means 12 may perform transmission by using electric power reachable to the first-sensor-data reception means 22 distant by an interval between right and left insoles worn by a wearer. For such short-range communication, for example, Wi-Fi®, Bluetooth®, near field communication (NFC), and infrared communication are usable. When short-range wireless communication is used, communication can be performed with small power consumption, compared with a case of using medium-range and long-range wireless communication.

First sensor data transmitted from the first-sensor-data transmission means 12 and received in the first-sensor-data reception means 22 are aggregated with second sensor data by the data processing means 23 and the aggregated data are processed. Processing executed by the data processing means 23 can be configured, for example, as processing of collectively transmitting first sensor data and second sensor data to an external device including a control unit that controls data and as processing of executing a predetermined operation.

As described above, according to the present example embodiment, even when being located in a location distant from a control unit that processes data, an insole-type electronic device can execute processing of acquiring data relating to a biological activity. As in PTL 2, power consumption can be reduced, compared with a configuration in which each of two insoles performs wireless communication to a control unit.

Second Example Embodiment

Figure 2:
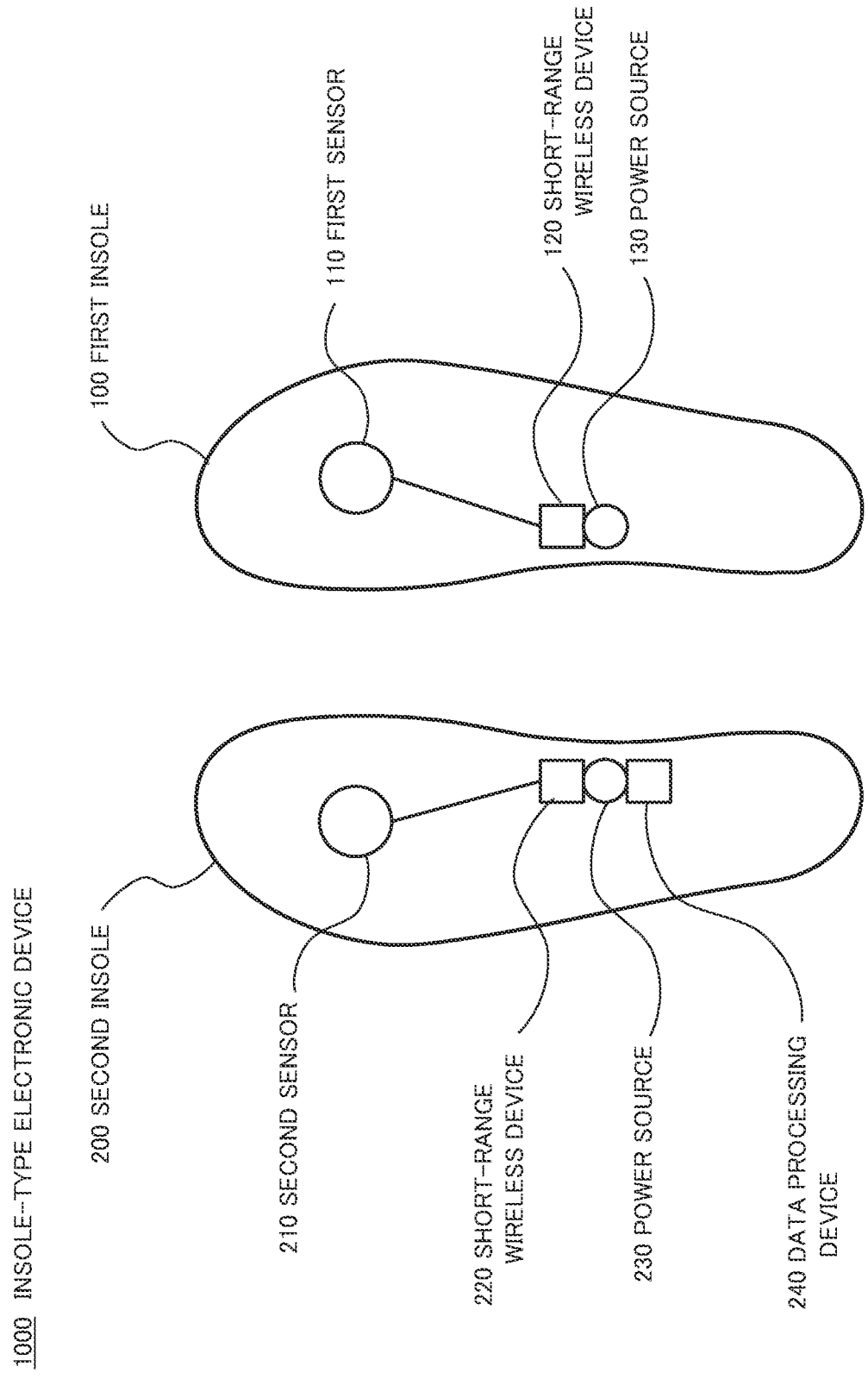
FIG. 2 is a block diagram illustrating an insole-type electronic device according to a second example embodiment.

According to the present example embodiment, a specific configuration of the insole-type electronic device according to the first example embodiment is described. FIG. 2 is a block diagram illustrating an insole-type electronic device 1000 according to the present example embodiment. The insole-type electronic device 1000 includes a first insole 100 and a second insole 200. In the following description, it is assumed that the first insole 100 is used for one's right foot and the second insole 200 is used for one's left foot, but it is not problematic that conversely, a first insole is used for one's left foot and a second insole is used for one's right foot.

The first insole 100 includes a first sensor 110, a short-range wireless device 120, and a power source 130. The first sensor 110 acquires, as first sensor data, a signal relating to a biological activity occurring in a first foot. The first sensor may be one sensor or may be configured by using a plurality of sensors. Herein, a signal relating to a biological activity includes, for example, a load applied to a sole, a temperature of a foot, and an acceleration of a foot. The short-range wireless device 120 transmits, by using short-range wireless communication, first sensor data to the second insole 200. For short-range wireless communication, for example, Wi-Fi®, Bluetooth®, NFC, and infrared communication are usable. When short-range wireless communication is used, communication can be performed with small power consumption, compared with a case of using medium-range and long-range wireless communication.

The power source 130 supplies electric power to the short-range wireless device 120. When the first sensor 110 is a sensor requiring electric power, electric power is supplied also to the first sensor 110. For the power supply 130, for example, a battery is usable. When the short-range wireless device 120 and the power supply 130 are disposed in an arch portion and a heel end of the first insole 100, a load received from a foot can be decreased and a sense of discomfort felt by a wearer can be reduced.

The second insole 200 includes a second sensor 210, a short-range wireless device 220, a power supply 230, and a data processing device 240. The second sensor 210 acquires, as second sensor data, a signal relating to a biological activity occurring in a second foot. The second sensor may be one sensor or may be configured by using a plurality of sensors. The short-range wireless device 220 receives first sensor data transmitted from the short-range wireless device 120. The power source 230 supplies electric power to the short-range wireless device 220 and the data processing device 240. When the second sensor 210 is a sensor requiring electric power, electric power is supplied also to the second sensor 210. For the power supply 230, for example, a battery is usable. When the whole or part of the short-range wireless device 220, the power supply 230, and the data processing device 240 are disposed in an arch portion and a heel end of the second insole 200, a load received from a foot can be decreased and a sense of discomfort felt by a wearer can be reduced. The data processing device 240 aggregates first sensor data and second sensor data and processes the aggregated data. While an example of specific processing is described later, for example, processing of collectively transmitting first sensor data and second sensor data to an external device and processing of executing a predetermined operation are conceivable.

Figure 3:
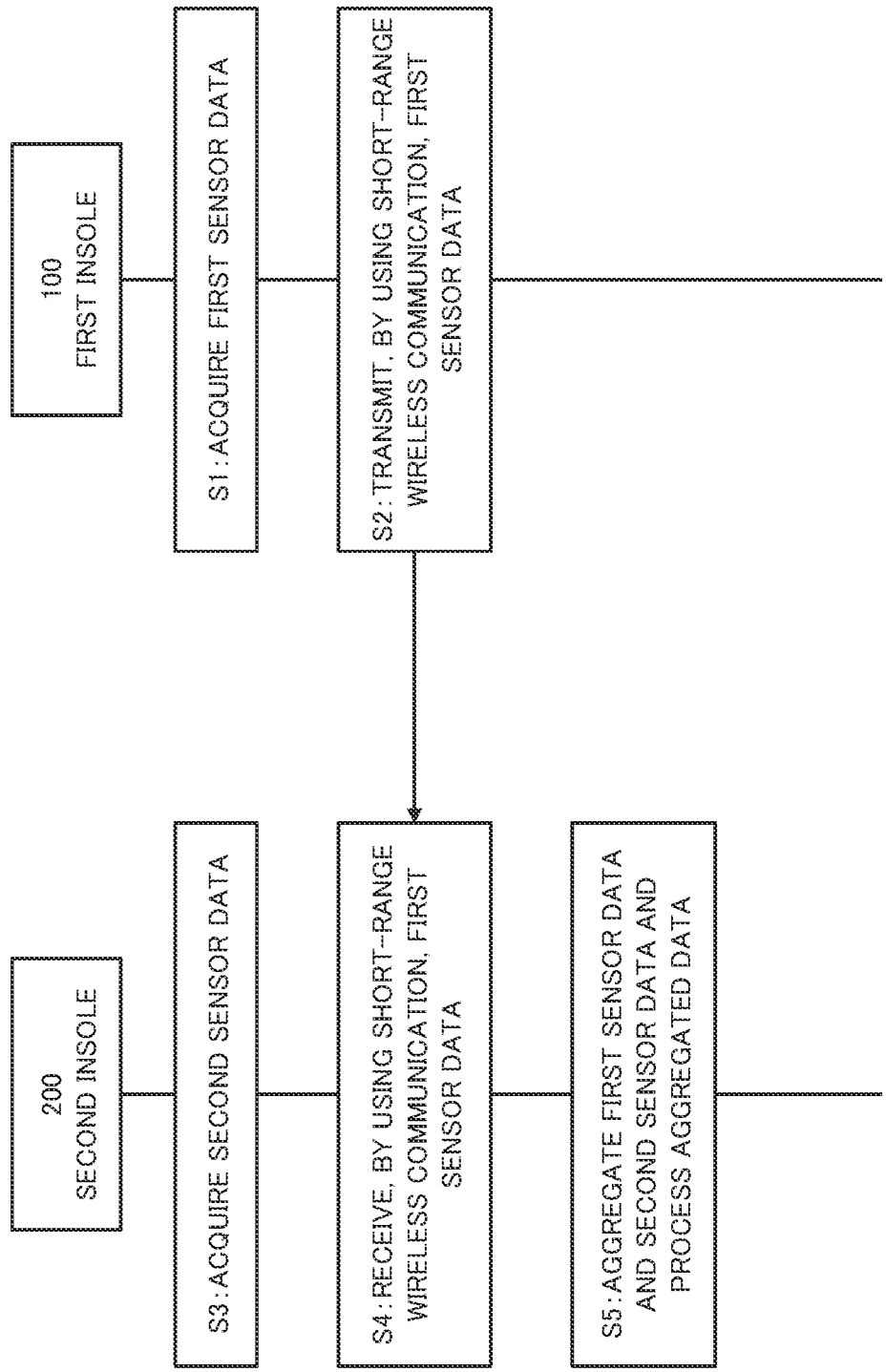
FIG. 3 is a sequence diagram illustrating an operation of the insole-type electronic device according to the second example embodiment.

FIG. 3 is a sequence diagram illustrating an operation of the insole-type electronic device 1000. First, the first insole 100 acquires first sensor data (S1). By using short-range wireless communication, the first insole 100 transmits the first sensor data to the second insole 200 (S2). The second insole 200 acquires second sensor data (S3). The second insole 200 also receives, by using short-range wireless communication, the first sensor data (S4). Note that an order of S3 and S4 is reversible. Next, the first sensor data and the second sensor data are aggregated and the aggregated data are processed (S5). According the operation, first sensor data are transmitted, by using short-range wireless communication, to the second insole 200, the first sensor data and second sensor data are aggregated, and the aggregated data are processed. Therefore, power consumption can be reduced, compared with a method in which two insole devices, i.e. right and left insole devices separately execute data processing.

Example 1

Figure 4:
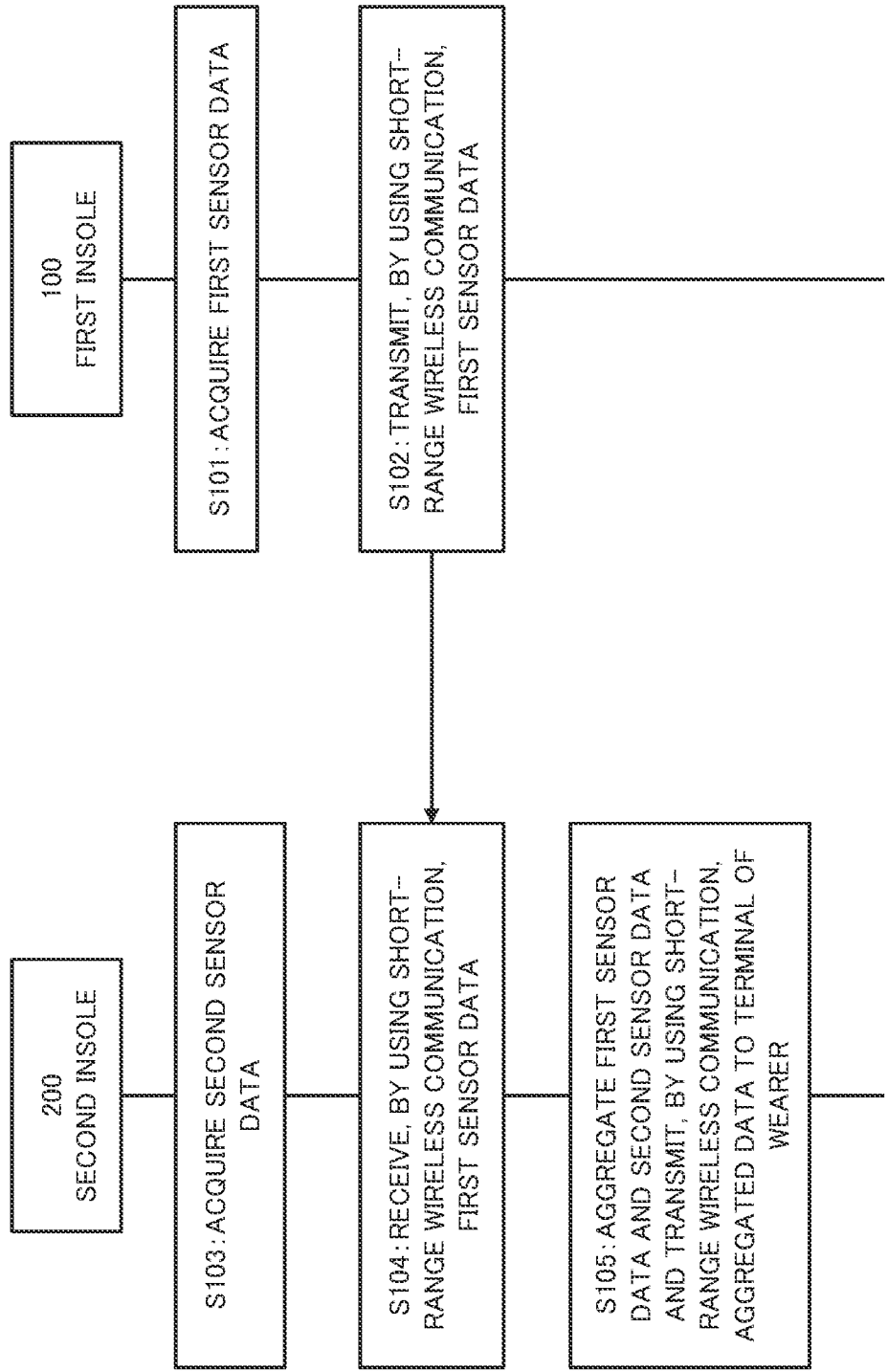
FIG. 4 is a sequence diagram illustrating another operation of the insole-type electronic device according to the second example embodiment.

According to the present example, a specific example of data processing is described. FIG. 4 is a sequence diagram illustrating the operation. First sensor data are acquired (S101) and by using short-range wireless communication, the first sensor data are transmitted to a second insole 200 (S102), and the second insole 200 acquires second sensor data (S103) and receives the first sensor data (S104). The processing is similar to the processing from S1 to S4 in FIG. 3. Next, a data processing device 240 transmits, by using short-range wireless communication, the first sensor data and the second sensor data to a terminal carried by a wearer (S105). As the terminal, for example, an electronic device such as a smartphone and a tablet computer is usable. The terminal can transfer, by using medium-to-long-range wireless communication, received data to a server and calculate, based on a local operation, desired data relating to a biological activity.

Example 2

Figure 5:
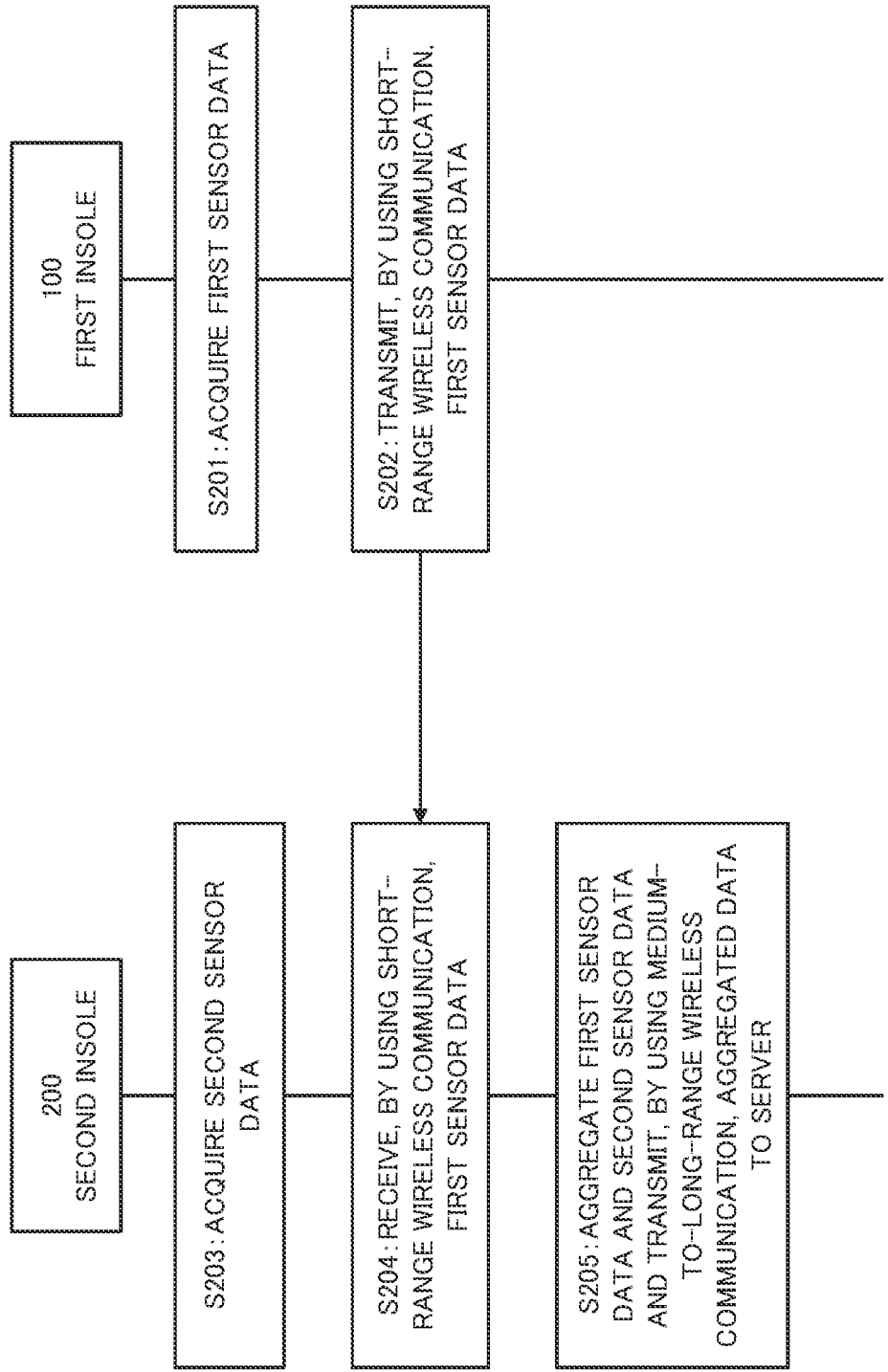
FIG. 5 is a sequence diagram illustrating still another operation of the insole-type electronic device according to the second example embodiment.

According to the present example, a specific example of an operation in which a data processing device 240 includes a medium-to-long-range communication function is described. FIG. 5 is a sequence diagram illustrating the operation. Similarly to the example 1, first sensor data are acquired (S201) and by using short-range wireless communication, the first sensor data are transmitted to a second insole 200 (S202), and the second insole 200 acquires second sensor data (S203) and receives the first sensor data (S204). Next, the data processing device 240 transmits, by using medium-to-long-range wireless communication, the first sensor data and the second sensor data to an external device such as a server. According to the present example, even when a wearer of an insole-type electronic device 1000 does not carry a terminal, first sensor data and second sensor data can be transmitted to an external device.

Example 3

According to the present example, an example in which a first sensor and a second sensor are a pressure sensor or a load sensor and a load applied to a sole portion is measured, and thereby a base-portion gravity position is calculated is described. Herein, it is assumed that a base portion indicates sole portions of both feet and a region inside the sole portions.

FIG. 6 is a block diagram illustrating an insole-type electronic device 1001. With regard to a measurement unit, a first insole 100 includes, as a first sensor, a pressure sensor 111 disposed on an anterior side of a sole and a pressure sensor 112. Similarly, a second insole 200 includes a pressure sensor 211 disposed on an anterior side of a sole and a pressure sensor 212. A base portion 300 in this case includes the first insole 100, the second insole 200, and a region between both insoles. When one pressure sensor is provided each for one foot, a base-portion gravity position 310 can be calculated, but in order to calculate an accurate base-portion gravity position 310, it is desirable to dispose two or more pressure sensors for one foot. The pressure sensors 111 and 112 and a short-range wireless device 120 are electrically connected and the pressure sensors 211 and 212 and a data processing device 241 are electrically connected, but in FIG. 6, illustration of wiring is omitted.

In calculation of a base-portion gravity, for example, first, the pressure sensors 111 and 112 each acquire, as first sensor data, a pressure applied to each of the sensors and transmit the data from the short-range wireless device 120 to a short-range wireless device 220. In contrast, in the second insole 200, the pressure sensors 211 and 212 each acquire, as second sensor data, a pressure applied to each of the sensors. The first sensor data and the second sensor data are aggregated in the data processing device 241.

Calculation of a base-portion gravity position 310 using aggregated data can be executed, for example, by the following three methods. A first method is a method of performing, similarly to the example 1, by using short-range wireless communication, transmission to a terminal carried by a wearer of an insole-type electronic device 1001. The terminal can calculate, by using received data, the base-portion gravity position 310 and calculate, by transferring data, the base-portion gravity position 310 by using a server or the like of a transfer destination.

A second method is a method enabled when the data processing device 241 includes a medium-to-long-range wireless function. Similarly to the example 2, aggregated data are transmitted, by using medium-to-long-range wireless communication, to an external device such as a server, and thereby the base-portion gravity position 310 can be calculated by using a server or the like.

A third method is a method enabled when the data processing device 241 includes an operation function. The data processing device 241 calculates a base-portion gravity position 310 from aggregated data. Data of the calculated base-portion gravity position 310 can be transmitted to a terminal carried by a wearer of an insole-type electronic device 1001, an external server, or the like.

Example 4

According to the present example, an insole-type electronic device capable of calculating a gravity position of each of one's right foot and one's left foot is described. FIG. 7 is a block diagram illustrating an insole-type electronic device 1002 according to the present example. A first insole 100 includes a pressure sensor 111 on an anterior inside of a foot, a pressure sensor 112 on a posterior side of the foot, and a pressure sensor 113 on an anterior outside of the foot. Similarly, a second insole 200 includes a pressure sensor 211 on an anterior inside of a foot, a pressure sensor 212 on a posterior side of the foot, and a pressure sensor 213 on an anterior outside of the foot. The pressure sensors 111, 112, and 113 and a short-range wireless device 120 are electrically connected and the pressure sensors 211, 212, and 213 and a data processing device 242 are electrically connected, but in FIG. 7, illustration of wiring is omitted.

First sensor data acquired in the pressure sensors 111, 112, and 113 are transmitted from the short-range wireless device 120 to a short-range wireless device 220 disposed in the second insole 200. In contrast, in the pressure sensors 211, 212, and 213, a pressure applied to each of the sensors is acquired as second sensor data. The first sensor data and the second sensor data are aggregated in the data processing device 242. The data processing device 242 can determine a right-foot gravity position 311, a left-foot gravity position 312, and a base-portion gravity position 310, by using three methods similar to the example 3, i.e. by transmitting aggregated data to a terminal of a wearer, transmitting aggregated data to a server or the like, and locally executing calculation.

Example 5

According to the examples 3 and 4, a configuration of detecting, by using a pressure sensor, a load applied to a sole was described, but by using another sensor, other data relating to a biological activity of a foot can be acquired. For example, a temperature sensor is used for a first sensor and a second sensor, and thereby a temperature (body temperature) of a sole portion can be measured.

FIG. 8 is a block diagram illustrating a configuration of an insole-type electronic device 1003 according to the present example. A temperature sensor 114 is disposed in a first insole 100, and a temperature sensor 214 is disposed in a second insole 200. The temperature sensor 114 and a short-range wireless device 120 are electrically connected and the temperature sensor 214 and a data processing device 243 are electrically connected, but in FIG. 8, illustration of wiring is omitted.

The temperature sensor 114 acquires, as first sensor data, a temperature of a right sole portion, and the temperature sensor 214 acquires, as second sensor data, a temperature of a left sole portion. The first sensor data are transmitted from the short-range wireless device 120 to a short-range wireless device 220. The first sensor data and the second sensor data are aggregated in the data processing device 243. The data processing device 243 can determine a temperature of the right sole portion and a temperature of the left sole portion, by using three methods similar to the example 3, i.e., by transmitting aggregated data to a terminal of a wearer, transmitting aggregated data to a server or the like, and locally executing calculation. Temperatures of a right sole portion and a left sole portion are determined, and thereby abnormality of a body temperature such as fever and hypothermia, abnormality of each of feet, and the like can be early found. In the example of FIG. 8, an example in which one temperature sensor is disposed for each of the first insole 100 and the second insole 200 was illustrated, but two or more temperature sensors may be disposed.

Example 6

When for a first sensor and a second sensor, an acceleration sensor is used, information relating to motions of both right and left feet can be acquired. FIG. 9 is a block diagram illustrating a configuration of an insole-type electronic device 1004 according to the present example. An acceleration sensor 115 is disposed in a first insole 100, and an acceleration sensor 215 is disposed in a second insole 200. The acceleration sensor 115 and a short-range wireless device 120 are electrically connected and the acceleration sensor 215 and a data processing device 244 are electrically connected, but in FIG. 9, illustration of wiring is omitted.

The acceleration sensor 115 acquires, as first sensor data, an acceleration of one's right foot, and the acceleration sensor 215 acquires, as second sensor data, an acceleration of one's left foot. The first sensor data are transmitted from the short-range wireless device 120 to a short-range wireless device 220. Next, the first sensor data and the second sensor data are aggregated in the data processing device 244. The data processing device 244 can determine information relating to motions of both right and left feet, by using three methods similar to the examples 3 and 4, i.e. by transmitting aggregated data to a terminal of a wearer, transmitting aggregated data to a server or the like, and locally executing calculation. For example, from data of accelerations of both right and left feet, motions of both right and left feet can be analyzed. In this case, a calculation amount is large, and therefore when aggregated data are transmitted from the data processing device 244 to a terminal carried by a wearer, the data are transferred from the terminal to a server, and the transferred data are analyzed by the server, analysis can be performed without a load on the data processing device 244 and the terminal. In the example of FIG. 9, an example in which one acceleration sensor is disposed for each of the first insole 100 and the second insole 200 was illustrated, but two or more acceleration sensors may be disposed.

As described above, according to the present example embodiment, even when being located in a location distant from a control unit that processes data, an insole-type electronic device can execute processing of acquiring data relating to a biological activity. Data relating to biological activities acquired in two insoles are aggregated by using short-range wireless communication and the aggregated data are processed, and therefore an insole-type electronic device having small power consumption can be provided.

Third Example Embodiment

While a sensor, a short-range wireless device, and a data processing device being components of the insole-type electronic device according to the second example embodiment can be installed in any location of an insole, these components are desirably disposed in a location where a wearer does not feel a sense of discomfort. According to the present example embodiment, a configuration example of an insole suitable for this desire is described. FIG. 10 is a perspective view illustrating a part of an insole-type electronic device 1005 according to the present example embodiment. In a second insole 200a, a heel cup 201 (an inclined portion) extending upward from a main surface of the second insole 200a is provided in a portion of a heel end. When components such as a sensor and a data processing device are disposed in the heel cup 201 and an arch portion 202 relevant to an arch of a foot, a sense of strangeness felt by a wearer when an insole is worn may be unlikely to occur. In the example of FIG. 10, a data processing device 240 is incorporated in the heel cup 201. Note that while not illustrated, also, with regard to a first insole, a similar shape is formed, and thereby a short-range wireless device and a power source can be disposed in an arch portion and a heel cup.

While the invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims.

The whole or part of the example embodiments disclosed above can be described as, but not limited to, the following supplementary notes.

(Supplementary Note 1)
An insole-type electronic device including:
a first insole including a first sensor that measures biological activity data of a first foot; and
a second insole including a second sensor that measures biological activity data of a second foot, wherein
the first insole includes
a first-sensor-data transmission means for transmitting first sensor data acquired by the first sensor to the second insole, and
the second insole includes
a first-sensor-data reception means for receiving the first sensor data and
a data processing means for processing second sensor data acquired by the second sensor and the first sensor data received by the first-sensor-data reception means.

(Supplementary Note 2)
The insole-type electronic device according to supplementary note 1, wherein
the data processing means includes
a data transfer means for transferring the first sensor data and the second sensor data to an external device.

(Supplementary Note 3)
The insole-type electronic device according to supplementary note 2, wherein
the data transfer means includes
a short-range wireless-communication means for transmitting the first sensor data and the second sensor data to an electronic device carried by a wearer of the first insole and the second insole.

(Supplementary Note 4)
The insole-type electronic device according to any one of supplementary notes 1 to 3, wherein
the first sensor and the second sensor each include a pressure sensor.

(Supplementary Note 5)
The insole-type electronic device according to supplementary note 4, wherein
the first sensor and the second sensor each include a plurality of pressure sensors.

(Supplementary Note 6)
The insole-type electronic device according to supplementary note 4 or 5, wherein
the data processing means includes
a base-portion-gravity calculation means for calculating, based on the first sensor data and the second sensor data, a base-portion gravity position and
a base-portion-gravity-position transmission means for transmitting the base-portion gravity position to an external device.

(Supplementary Note 7)
The insole-type electronic device according to any one of supplementary notes 1 to 6, wherein
the first sensor and the second sensor each include a temperature sensor.

(Supplementary Note 8)
The insole-type electronic device according to any one of supplementary notes 1 to 7, wherein
the first sensor and the second sensor each include an acceleration sensor.

(Supplementary Note 9)
The insole-type electronic device according to any one of supplementary notes 1 to 8, wherein
at least one of whether the first-sensor-data transmission means is disposed in an arch portion or a heel end of the first insole or whether at least one of the first-sensor-data reception means or the data processing means is disposed in an arch portion or a heel end of the second insole is satisfied.

(Supplementary Note 10)
A control method for an insole-type electronic device, the method including:
acquiring, by a first sensor disposed in a first insole, first sensor data relating to a biological activity of a first foot;
acquiring, by a second sensor disposed in a second insole, second sensor data relating to a biological activity of a second foot;
transmitting the first sensor data to the second insole;
receiving, by the second insole, the first sensor data; and
processing, by a data processing means included in the second insole, the first sensor data and the second sensor data.

(Supplementary Note 11)
The control method for an insole-type electronic device according to supplementary note 10, the method further including,
by the data processing means,
transferring the first sensor data and the second sensor data to an external device.

(Supplementary Note 12)
The control method for an insole-type electronic device according to supplementary note 11, the method further including
transmitting, by using short-range wireless communication, the first sensor data and the second sensor data to an electronic device carried by a wearer of the first insole and the second insole.

(Supplementary Note 13)
The control method for an insole-type electronic device according to any one of supplementary notes 10 to 12, wherein
the first sensor and the second sensor each include a pressure sensor.

(Supplementary Note 14)
The control method for an insole-type electronic device according to supplementary notes 13, wherein
the first sensor and the second sensor each include a plurality of pressure sensors.

(Supplementary Note 15)
The control method for an insole-type electronic device according to supplementary note 13 or 14, the method further including:
by the data processing means,
calculating, based on the first sensor data and the second sensor data, a base-portion gravity position; and
transmitting the base-portion gravity position to an external device.

(Supplementary Note 16)
The control method for an insole-type electronic device according to any one of supplementary notes 10 to 15, wherein
the first sensor and the second sensor include temperature sensors and
acquire a temperature of the first foot and a temperature of the second foot, respectively.

(Supplementary Note 17)
The control method for an insole-type electronic device according to any one of supplementary notes 10 or 16, wherein
the first sensor and the second sensor include acceleration sensors and acquire an acceleration of the first foot and an acceleration of the second foot, respectively.

The previous description of embodiments is provided to enable a person skilled in the art to make and use the present invention. Moreover, various modifications to these example embodiments will be readily apparent to those skilled in the art, and the generic principles and specific examples defined herein may be applied to other embodiments without the use of inventive faculty.

Therefore, the present invention is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

The invention claimed is:

1. An insole-type electronic device comprising:
   a first insole including a first sensor that acquires first sensor data relating to a biological activity of a first foot; and
   a second insole including a second sensor that acquires second sensor data relating to a biological activity of a second foot, wherein
   the first insole includes a first-sensor-data transmitter transmitting the first sensor data to the second insole,
   the second insole includes a first-sensor-data receiver receiving the first sensor data, and a data processor calculating a base-portion gravity position based on the first sensor data and the second sensor data,
   the first sensor and the second sensor each include a pressure sensor, and
   the data processor includes a base-portion-gravity-position transmitter transmitting the base-portion gravity position to an external device.

2. The insole-type electronic device according to claim 1, wherein
   the first sensor and the second sensor each include a temperature sensor.

3. An insole-type electronic device comprising:
   a first insole including a first sensor that acquires first sensor data relating to a biological activity of a first foot; and
   a second insole including a second sensor that acquires second sensor data relating to a biological activity of a second foot, wherein
   the first insole includes a first-sensor-data transmitter transmitting the first sensor data to the second insole,
   the second insole includes a first-sensor-data receiver receiving the first sensor data, and a data processor processing the first sensor data and the second sensor data,
   at least one of a first condition and a second condition are satisfied,
   the first condition is that the first-sensor-data transmitter is disposed in an arch portion or a heel end of the first insole, and
   the second condition is that at least one of the first-sensor-data receiver or the data processor is disposed in an arch portion or a heel end of the second insole.

4. A control method for an insole-type electronic device, the method comprising:
   acquiring, by a first sensor disposed in a first insole, first sensor data relating to a biological activity of a first foot, wherein the first sensor data is first pressure on the first insole;
   acquiring, by a second sensor disposed in a second insole, second sensor data relating to a biological activity of a second foot, wherein the second sensor data is second pressure on the second insole;
   transmitting the first sensor data to the second insole;
   receiving, by the second insole, the first sensor data; and
   calculating, by a data processor included in the second insole, a base-portion a base-portion gravity position based on the first sensor data and the second sensor data.

5. The control method for an insole-type electronic device according to claim 4, the method further comprising,
   transferring, by the data processor, the first sensor data and the second sensor data to an external device.

6. The insole-type electronic device according to claim 1, wherein
   the data processor includes a data transfer device transferring the first sensor data and the second sensor data to the external device.

7. The insole-type electronic device according to claim 1, wherein
   the first sensor and the second sensor each include a plurality of pressure sensors.

8. The insole-type electronic device according to claim 6, wherein
   the data transfer device includes
   a short-range wireless-communicator transmitting the first sensor data and the second sensor data to an electronic device carried by a wearer of the first insole and the second insole.

9. The insole-type electronic device according to claim 8, wherein
   the first sensor and the second sensor each include a plurality of pressure sensors.

10. The insole-type electronic device according to claim 3, wherein
    the data processor includes
    a data transfer device transferring the first sensor data and the second sensor data to an external device.

11. The insole-type electronic device according to claim 10, wherein
    the data transfer device includes
    a short-range wireless-communicator transmitting the first sensor data and the second sensor data to an electronic device carried by a wearer of the first insole and the second insole.

12. The insole-type electronic device according to claim 3, wherein
    the first sensor and the second sensor each include a pressure sensor.

13. The insole-type electronic device according to claim 12, wherein
    the first sensor and the second sensor each include a plurality of pressure sensors.

14. The insole-type electronic device according to claim 3, wherein
    the data processor calculates, based on the first sensor data and the second sensor data, a base-portion gravity position, and
    the data processor includes a base-portion-gravity-position transmitter transmitting the base-portion gravity position to an external device.

15. The insole-type electronic device according to claim 14, wherein
the first sensor and the second sensor each include a temperature sensor.

\* \* \* \* \*